(12) United States Patent
Beyens et al.

(10) Patent No.: US 10,359,343 B2
(45) Date of Patent: Jul. 23, 2019

(54) IMMERSION DEVICE FOR SLAG SAMPLE COLLECTION

(71) Applicant: Heraeus Electro-Nite International N.V., Houthalen (BE)

(72) Inventors: Dries Beyens, Kinrooi (BE); Paul A. Turner, Milwaukee, WI (US)

(73) Assignee: Heraeus Electro-Nite International N.V., Houthalen (BE)

( * ) Notice: Subject to any disclaimer, the term of this patent is extended or adjusted under 35 U.S.C. 154(b) by 112 days.

(21) Appl. No.: 15/701,846

(22) Filed: Sep. 12, 2017

(65) Prior Publication Data

US 2018/0073962 A1     Mar. 15, 2018

Related U.S. Application Data

(60) Provisional application No. 62/393,727, filed on Sep. 13, 2016.

(30) Foreign Application Priority Data

Sep. 13, 2016 (EP) .................................... 16188557

(51) Int. Cl.
    *G01N 33/205*     (2019.01)
    *G01N 1/12*     (2006.01)
    (Continued)

(52) U.S. Cl.
    CPC ............ *G01N 1/2035* (2013.01); *G01N 1/125* (2013.01); *G01N 33/205* (2019.01); *C21C 5/28* (2013.01)

(58) Field of Classification Search
    CPC ..... G01N 1/2035; G01N 33/205; G01N 1/205
    (Continued)

(56) References Cited

U.S. PATENT DOCUMENTS 4,291,585 A    9/1981   Kolb et al.
5,415,052 A    5/1995   Baerts
(Continued)

FOREIGN PATENT DOCUMENTS

WO     2011047846 A1    4/2011
WO     WO-2011047846 A1 *   4/2011 ............... C21B 7/24

OTHER PUBLICATIONS

Extended Search Report dated Mar. 31, 2017 in EP Application No. 16188557.9.

*Primary Examiner* — Justin Seo
*Assistant Examiner* — Jean F Morello
(74) *Attorney, Agent, or Firm* — Panitch Schwarze Belisario & Nadel LLP

(57) ABSTRACT

An immersion device for collecting a slag sample and measuring a molten metal parameter is provided. The immersion device includes an inflow conduit for directing the molten slag to a slag sample chamber and a measuring element for measuring the parameter of the molten metal. The inflow conduit and the measuring element are arranged in the top area of an immersion end of the immersion device and/or are facing towards an immersion direction. During immersion in the immersion direction into the molten slag and then the molten metal, the molten slag enters an external portion of the inflow conduit and is directed through an inner portion of the inflow conduit to the slag sample chamber. Reliable slag collection and molten metal measurement also in a converter can thereby be achieved. A method of collecting a slag sample and measuring a molten metal parameter is also provided.

14 Claims, 3 Drawing Sheets

(51) Int. Cl.
*G01N 1/20* (2006.01)
*C21C 5/28* (2006.01)

(58) Field of Classification Search
USPC ........................................................ 73/864.53
See application file for complete search history.

(56) References Cited

U.S. PATENT DOCUMENTS

| | | |
|---|---|---|
| 5,435,196 A | 7/1995 | Cassidy |
| 5,577,841 A | 11/1996 | Wall |
| 6,370,973 B1 | 4/2002 | Wunsch et al. |
| 6,581,482 B2 * | 6/2003 | Cappa ...................... C21B 7/24 |
| | | 73/864.53 |
| 7,621,191 B2 | 11/2009 | Knevels et al. |
| 7,832,294 B2 | 11/2010 | Neyens |
| 9,176,027 B2 | 11/2015 | Neyens et al. |
| 2007/0137324 A1 | 6/2007 | Neyens |
| 2012/0082183 A1 | 4/2012 | Beyens |
| 2013/0098173 A1 * | 4/2013 | Neyens ................... B22D 2/00 |
| | | 73/864.51 |
| 2014/0119404 A1 | 5/2014 | Beyens |
| 2016/0209341 A1 | 7/2016 | Turner et al. |

\* cited by examiner

IMMERSION DEVICE FOR SLAG SAMPLE COLLECTION

CROSS-REFERENCE TO RELATED APPLICATIONS

This application claims the benefit of U.S. Provisional Patent Application No. 62/393,727, filed Sep. 13, 2016, the entire contents of which are incorporated by reference herein.

BACKGROUND OF THE INVENTION

The invention relates to an immersion device for collecting a slag sample and measuring a molten metal parameter, as well as a method for collecting a slag sample and measuring a molten metal parameter.

In most molten metal refining processes, particularly processes for making steel, a molten slag is produced forming a layer above the molten metal. Molten slag has a lower density than the molten metal. Because of this, the molten slag floats and accumulates above the surface of the molten metal that is commonly located within a processing vessel. The slag provides for essential metallurgical functions such as the absorption of certain elements desired to be removed from the molten metal or the creation of a reaction environment in which elements such as carbon are oxidized in the molten slag and released as a gaseous byproduct of the reaction.

In the metal making industry, it is important to monitor the chemical and/or metallurgical composition of the refining slag in order to effectively monitor the molten metal processing, to compare initial calculated chemistry to actual composition to update charge mass and material balance models and to efficiently collect and timely analyze the slag in order to particular properly control the metal refining process.

A traditional method for obtaining a sample of metal refining slag from a molten metal bath in a processing vessel is to immerse a metal object, such as a pipe, a metal spoon, a metal chain or the like into the slag for a predetermined relatively short period of time. A layer of the molten slag is chilled onto the cooler metal object so that upon removal of the metal object from the processing vessel, the solid slag may be conveniently broken away from the metal object, collected and promptly analyzed using known analytical methods and techniques.

This method has the disadvantage of an unsecured sample composed of the broken smaller pieces which at times can be mixed at the collection location with broken bits of slags of a previous process batch. Securing the frozen slag collecting process, such as taught in U.S. Pat. No. 6,370,973, employs a funnel 4 to direct the liquid slag 31 through a mold inlet 3 to a sample chamber 2 with a cooling plate 5 to obtain a slag sample after removal from the sample chamber 2.

It is also common in the metal producing industry to monitor various other qualities of the molten metal in a processing vessel such as temperature, temperature of solidification, dissolved oxygen and to obtain physical samples to ascertain other component contents. Many different types of devices or probes have been developed and used for this purpose, such as disclosed in U.S. Pat. No. 7,832,294. Typically, a measuring head containing sensing elements is mounted upon a carrier tube, typically a cardboard tube, and immersed into the molten metal bath. The cardboard tube supports the measuring head and/or samplers allowing the sensors and/or samplers to be inserted into the molten metal at a desired depth below the molten slag to obtain the necessary data and/or physical sample. When a sample of the slag floating upon the molten metal is desired, it has been known to extract a physical sample into an inflow conduit located on the side of the hollow carrier tube, such as taught by U.S. Pat. Nos. 5,415,052 and 9,176,027. Alternatively, it has been known to secure generally cylindrical metal shapes to the cardboard tube such as metal tubes or metal coils at a stationary position, such as in U.S. Pat. No. 5,435,196 or 7,621,191. In this manner, when the probe body is inserted or immersed into the molten metal bath for making the required measurement at the tip during refining, a sample of the slag can be simultaneously obtained at the side and recovered when the probe body is removed from the metal bath.

While these methods of obtaining slag samples can be useful in some applications, it is commonly difficult to use because it requires to adapt the immersion process to the exact location of the slag and its depth, so that the metal object used for collecting the sample of the slag is, in fact, maintained in the slag layer and does not pass through the slag into the molten metal below the slag layer.

A further problem is related with slag sample collection from a converter for producing steel. A converter is a furnace for producing steel from iron as well as scrap iron, steel and/or iron with impurities. Molten iron is added to the scrap iron, iron and/or steel with impurities. A high pressure stream of oxygen and particularly powdered lime is blown through the mixture, causing chemical reactions and removing some of the carbon from the iron. The amount of carbon removed from the iron determines the quality or grade of steel produced. This part of the process is monitored carefully until the percentage of carbon is reduced to the correct level according to the type of steel required. The slag of a converter, i.e. converter slag, is continuously in motion, contains gas components and has a fluidity that varies widely during the converter process. Therefore, slag sample collection is generally difficult and sometimes not even possible with devices configured for slag from a refiner; i.e. refiner slag.

International Patent Application Publication No. WO 2011/047846 describes this issue and the particular difficulties during taking slag samples from a converter due to the different properties of converter slag and the special converter conditions compared to all other slag sampling processes, such as, for example, refiner slag. Page 2, lines 5 to 13 of International Patent Application Publication No. WO 2011/047846 describes that a serious problem with taking slag samples from a converter is that the slag because of poor fluidity will not flow into a sample chamber with a small inlet channel as used in taking slag samples from for instance pig iron. For that reason, the sample chamber has to have a large inlet opening. With a sample chamber having a sectional area which is determined by the inner sectional area of the probe used with the sub-lance system to take a sample, the size of the inlet opening is in the range of at least half of that sectional area to equal to the sectional area of the sample chamber. However, with a large inlet opening it is a problem to keep the slag in the sample chamber.

Nowadays, a probe for collecting a slag sample from a steelmaking converter is typically a multifunctional measuring probe that is not only able to collect slag samples, but also comprises one or more measuring elements for measuring properties of the molten metal during only one single immersion process. If obtaining only converter slag samples, one could select a wide inlet opening with a comparatively big diameter for reliable converter slag collection as taught in International Patent Application Publication No. WO 2011/047846 and U.S. Pat. No. 6,370,973.

In particular, it is targeted to collect a slag sample with at least a temperature measuring unit in the same sensor. The sensor is immersed in the bath by means of a sublance system. The vessel is a converter for steelmaking, mostly operated with a top blowing lance and bottom gas stirring.

However, conventional immersion probes have at least a thermocouple and as such there is typically only limited space available on the measuring head of such multifunctional measuring probes as, for example, illustrated in U.S. Pat. No. 9,176,027. This available space at the immersion end on the measuring head is particularly not enough for arranging the wide inlet openings, as taught in International Patent Application Publication No. WO 2011/047846 and U.S. Pat. No. 6,370,973, and, at the same time, all thermal mass at the measuring head can disturb the accuracy of the bath temperature measurement.

The contents of the cited documents are incorporated by reference herein. The above described features known from the prior art can be combined alone or in combination with one of the below disclosed aspects and embodiments of the present invention.

BRIEF SUMMARY OF THE INVENTION

An objective of the present invention is to provide a further developed device and method for collecting a slag sample and measuring a molten metal parameter.

The problem is solved by an immersion device for collecting a slag sample and measuring a molten metal parameter. The immersion device comprises an inflow conduit for directing the molten slag to a slag sample chamber and a measuring element for measuring the parameter of the molten metal. The inflow conduit comprises an external portion and an internal portion, and the inflow conduit and the measuring element are both arranged in the top area of an immersion end of the immersion device and/or both facing towards an immersion direction. The immersion device is composed such that, during immersion in the immersion direction into the molten slag and then the molten metal, the molten slag enters the external portion of the inflow conduit and is directed through the inner portion of the inflow conduit to the slag sample chamber.

The invention is based on the insight of the applicant that the available space in the top area next to or alongside of the measuring element—or measuring elements of a typical multifunctional measurement head for refiner molten metal measurement—can in fact be enough to arrange an inflow conduit in the top area of the immersion end and/or facing towards the immersion direction that is capable of reliably collecting a sample of molten converter slag without hindering or impeding the molten metal parameter measurement.

DETAILED DESCRIPTION OF THE INVENTION

Figure 1:
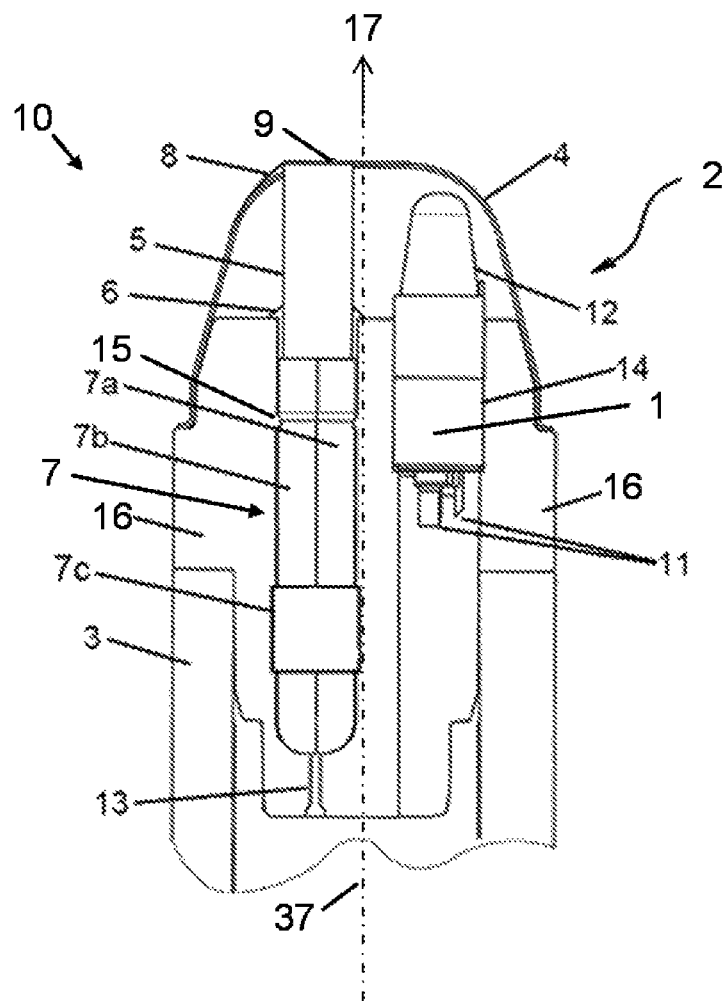
FIG. 1 shows a measuring head with one or multiple measuring elements mounted on a carrier tube, wherein an inflow conduit extends from the slag sample chamber to the exterior of the measuring head cap, in accordance with an embodiment of the present invention.

An immersion device is a device suitable for or configured to fulfill a dedicated function by getting or being immersed into molten slag and molten metal.

Molten metal is particularly molten iron. Molten metal within the meaning of the present application has a temperature above 1000° C. Molten iron has usually a temperature of more than 1500° C.

Collecting a slag sample means that molten slag is taken or flowing into the immersion device and taken out of the furnace together with the immersion device for subsequent analysis.

Molten metal parameter means a property of the molten metal such as present temperature, carbon content or concentration, and oxygen content or concentration. In particular, the molten metal parameter is measured during exposure of the measuring element to the molten metal.

Inflow conduit for directing the molten slag to a slag sample chamber means an entry channel that allows the molten slag to enter and/or to be directed inside of the immersion device. Particularly, the inflow conduit is a pipe or tube. The inflow conduit guides or conveys the molten slag to the sample chamber, which is preferably contained at least partially within a housing of the immersion device. Preferably, the slag sample chamber collects and cools the inflowing molten slag and/or secures the solidified slag. As such, the solidified slag is not subject to contamination from previous samples upon retrieval.

The term housing commonly refers to an embedding system.

Internal portion of the inflow conduit means the portion of an inflow conduit being embedded in the housing.

External portion of the inflow conduit means the portion of an inflow conduit not being embedded in the housing. In particular, an external portion of an inflow conduit commonly sticks out of the housing and/or is free standing.

Measuring element for measuring the parameter of the molten metal usually comprises a sensor for generating a signal during exposure to the molten metal, wherein the signal value corresponds to the property or parameter of the molten metal to be measured.

In particular, more than one measuring element is provided, preferably at least two or three or exactly two or three. A very efficient and/or simultaneous measurement of different molten metal parameters can thereby be achieved.

The measuring element usually comprises an electrical contact or interface for signal or data transfer and/or exchange with an analysis unit or storing unit. The measuring element can comprise an electronic component or circuit for signal or data processing. For example, a cable can thereby be connected to the measuring element for, e.g., real time display of the measured parameter during immersion of the immersion device.

Immersion end of the immersion device means the end of the immersion device facing the molten slag during immersion in immersion direction. In short, immersion end is the end of the immersion device directed in or towards immersion direction.

Immersion direction is commonly coaxial to the longitudinal axis of the immersion device. If the immersion device has a cylindrical or substantially cylindrical shape or a curved surface, the longitudinal axis and/or the immersion direction preferably corresponds to the respective central axis.

The immersion end of the immersion device comprises a top and a side. The top can comprise a tip as closest point or surface in immersion direction.

The top is what can be seen from top view particularly except the side boundaries. The side is what can be seen from side view, particularly except the top boundaries.

In particular, when the immersion end has a cylindrical shape, then the top is the top and the side is the curved surface.

Top area is an area of the immersion device in immersion direction close to and particularly including or bordered by the top surface or the tip of the immersion device. Area means sector, zone or region, thus not a surface but optionally including a surface.

In particular, top area refers to a section or part of the immersion device in immersion direction and/or along the longitudinal axis extending to the tip of the immersion device prior to immersion, the section or part being covered by the measuring head cap and/or having a length of less than the maximal outer diameter of the immersion device and/or a length of more than the diameter of the inflow conduit. The maximal outer diameter is commonly the maximal distance of two points of the curved surface of the immersion device prior to immersion.

Particularly, the top area does not include a side surface, curved surface or radial surface.

Particularly, the top area is limited by the housing surface in immersion direction, i.e., in longitudinal axis, the top area begins at or after the surface of the housing facing towards the immersion direction or the melting bath and ends at the tip of the measuring head, i.e. the maximal point in immersion direction.

In particular, an inflow conduit arranged in the top area is configured to collect molten slag from the top surface and particularly not from the side surface.

In particular, the inflow conduit and the measuring element both arranged in the top area of an immersion end of the immersion device refers to an inflow conduit and the measuring element being positioned inside of an inner area of a surface of a housing, thus not crossing an outer borderline or edge of the surface. Preferably, the surface is within the top area. Preferably, the surface is a plane or substantially plane surface.

Preferably, the surface is oriented orthogonal or substantially orthogonal to the longitudinal axis and/or the immersion direction. In particular, the inflow conduit and/or the measuring element may pass through the surface in or substantially in immersion direction.

In particular, a measuring element arranged in the top area is configured to measure a molten metal parameter by exposure to the molten metal at the top surface and not the side surface.

In particular, top surface is the present top surface during immersion. Depending on the material presently exposed to the molten slag and/or molten metal, the top surface can change due to removal of top surface material. Same particularly applies to the side surface.

Facing towards an immersion direction means configured to interact with molten slag and/or molten metal in immersion direction, thus not with molten slag or molten metal at the side surface.

Inflow conduit facing towards an immersion direction means that an opening of the inflow conduit is oriented in a way to allow molten slag in immersion direction to enter or flow into the opening, thus not from the side.

The inflow conduit does not necessarily extend in parallel to the immersion direction. Basically, the inflow conduit extending in parallel or substantially in parallel to the immersion direction, nevertheless, represents a preferred embodiment. In fact, the inflow conduit facing towards an immersion direction does not include an inflow conduit with an opening for inflow of molten slag being arranged entirely at a side surface.

Measuring element facing towards an immersion direction means that a sensor of the measuring element is configured or oriented in a way to only interact and/or measure molten metal in immersion direction, thus not from the side.

Not from the side means with respect to the inflow conduit and the measuring element that not included is slag or metal being at the side surface at the time of flowing into the inflow conduit or its opening or at the time of measurement by exposure to the measuring element or its sensor. Included within the meaning of "not from the side," however, are slag or metal that may flow from the side to the top and after reaching the top being collected there by the inflow conduit or being measured there by the measuring element.

By means of an immersion device for collecting a slag sample and measuring a molten metal parameter, wherein the immersion device comprising an inflow conduit for the molten slag and a measuring element for measuring the parameter of the molten metal, wherein the inflow conduit comprises an external portion and an internal portion, wherein the inflow conduit and the measuring element are both arranged in the top area of an immersion end of the immersion device and/or both facing towards an immersion direction, wherein the immersion device is composed such that during immersion in the immersion direction into the molten slag and then the molten metal, the molten slag enters the external portion of the inflow conduit and is directed through the inner portion of the inflow conduit to the slag sample chamber a very reliable collection of molten converter slag and molten metal measurement can be achieved.

U.S. Pat. No. 6,370,973 shows, in FIG. 4, an embodiment without an inflow conduit for slag comprising an external portion. Furthermore, the steel sample inlet at the tip is closed by a steel cap for protection against slag such that the immersion device of the embodiment is not composed such that molten slag could enter the external portion of the steel sample inlet.

The slag collection is also for converter slag very tolerant in terms of positioning of the immersion device relative to the molten metal surface. Furthermore, pure samples of slag can be obtained and pure molten metal can be measured, thus enabling to obtain high precision analysis and measurement results. In particular, an inflow conduit facing towards the immersion direction avoids exposure to gases from the burning cardboard tube thus avoiding contamination and a very pure slag sample.

In one embodiment, the inflow conduit is composed such that the inflow conduit can resist molten slag but melts upon exposure to molten metal.

Melt means liquefy, melt down and/or melt away including dissolving and entering into solution.

The inflow conduit can thereby convey or guide a molten slag flow into a chamber for storing the slag sample during passing the slag layer. When the molten metal is reached, the inflow conduit melts and thereby allows the contained slag to be flushed away from the top area by the molten metal bath.

The molten metal measurement can thereby be conducted without or without mentionable impact or impurity by the slag of the inflow conduit. Furthermore, a very pure slag sample can be collected without or almost without molten metal content.

The embodiment of having an inflow conduit composed such that the inflow conduit can resist molten slag but melts upon exposure to molten metal, is based on the insight that collecting converter slag is possible also with a comparatively small inflow conduit when facing in immersion direction due to the immersion force, and that dividing the slag sample collection and molten metal measurement into separate subsequent processes furthermore helps to obtain very little interference of the slag sample collection process and the molten metal measurement process.

Providing an inflow conduit composed such that the inflow conduit can resist molten slag but melts upon exposure to molten metal, a division of the slag sample collection and molten metal measurement into the separate subsequent processes.

In particular, melting away thus removes the slag inside the inflow conduit and also the inflow conduit immediately.

Preferably, the inflow conduit is composed to melt down upon exposure to the molten metal. Melting down means that the inflow conduit melts down to the surface of the housing.

This helps to obtain agglomerated melt of the inflow conduit that may work as closure for the slag sample chamber, thus reducing slag to escape from the slag sample chamber and to interfere the molten metal measurement.

In one embodiment, the external portion of the inflow conduit is free standing.

Free standing means not being embedded for example in a housing but mainly or entirely be spaced to adjacent members. Holding means or an interface to the measuring head cap having only a local contact with an area of less than 5% or at most 10% of the outer surface of the external portion of the inflow conduit should not be considered.

Having an external portion of the inflow conduit that is free standing allows improved melting down of the inflow conduit.

In one embodiment, the inflow conduit is composed to be present during molten slag collection and removed during the molten metal measurement. Thereby, slag does not interfere with the measuring elements and the molten metal measurement.

In one embodiment, the immersion device comprises a measuring element cap that covers the measuring element, wherein the measuring element cap is composed such that the measuring element cap melts upon exposure to the molten metal.

Cover means at least partly cover the measuring element or all measuring element, particularly towards immersion direction. Preferably, the measuring element cap covers the sensor of the measuring element in the immersion direction.

The molten metal measurement can thereby be conducted without or without mentionable impact or impurity by slag or the slag of the inflow conduit. The measurement element, especially the sensor, is moreover protected from other environmental conditions and substances within the immersion device in the top area before reaching the molten metal.

Preferably, the measuring element cap is composed to resist molten slag.

In one embodiment, the immersion device comprises a measuring head cap for covering the top area of the immersion device, wherein the measuring head cap is composed such that the measuring head cap can resist molten slag but melts upon exposure to the molten metal. The measuring head cap serves as a protection during transportation, handling and substantial impacts. The wall thickness of such a cap is typically 0.8 mm. In contact with slag, it will take several seconds to melt, while in contact with the molten metal, about 1 second to melt. The sensor is inserted into the converter by mechanical means typically with an entry speed of 30-60 cm/s. It remains stationary during 6-8 seconds and then leaves at a speed of about 20 cm/s.

As the immersion device is guided towards the molten slag surface, ambient heat of the metallurgical vessel increases the temperature of the measuring head cap of the immersion device. The cap thus avoids its chilling effect upon the slag.

Furthermore, slag is prevented from approaching the measuring element or the measuring element cap while slag is enabled to be guided to the slag cooling chamber. Hampering of the molten metal measurement due to slag interference can thus be well avoided.

Preferably, the measuring head cap is configured to the inflow conduit, the measuring element cap and/or the measuring element. In one embodiment, such covering or embracing may not include the end of the inflow opening of the inflow conduit when this flush with the top surface of the measuring head cap or when an cap opening of the measuring head cap is crossing the inflow opening of the inflow conduit.

Particularly, the outer surface of the measuring element cap is only exposed to gas or having a gap or distance to the inflow conduit and/or the measuring head cap.

Particularly, measuring head cap forms the top surface or the tip. Preferably, the measuring head cap has a length in immersion direction and/or in longitudinal axis of at least 20% of the length of the device head and/or at most half of the length of the device head, preferably about 30% of the length of the device head.

In one embodiment, the longitudinal axis of the immersion device runs coaxial or substantially coaxial to the immersion direction. Substantially coaxial can comprise an angle of within a range of minus 30° to plus 30°.

Preferably, the inflow conduit, the measuring element cap and/or the measuring head cap are arranged, designed and/or composed such that the measuring element cap and/or the measuring head cap melt down or away substantially at the same time or in the same moment as the inflow conduit melt down or away. Thereby, at least one measuring element can be exposed to the molten metal bath without or without mentionable impact or impurity by slag or the slag of the inflow conduit.

For iron or steel as metal, the inflow conduit, the measuring element cap and/or the measuring head cap are designed to melt down at about 1.5 thousand degree Celsius or 1500° C.

In particular, the inflow conduit, the measuring element cap and/or the measuring head cap are made of metal, particularly the same metal to reduce production expense. The temperature for melting down can be adjusted by reducing the wall thickness for a reduced melting down temperature and by increasing the wall thickness for an increased melting down temperature. Additionally or alternatively, a particular sort and/or grade of metal can be chosen to realize the needed melting down temperature.

Preferably, the inflow conduit, the measuring element cap and/or the measuring head cap are made of steel, more preferably low carbon steel. Low carbon steel is in particular of advantage for use in a steelmaking converter.

Preferably, the wall thickness of the inflow conduit, the measuring element cap and/or the measuring head cap is at least 0.5 mm and/or at most 3 mm, preferably 1.5 mm.

In particular, the measuring element cap and/or the measuring head cap have a conus shape body and/or a dome-shaped top. A particular low flow resistance in molten slag and molten metal as well as particular little material expense can be achieved.

In one embodiment, a cap opening of the measuring head cap is designed such that molten slag can flow through the cap opening into the inflow conduit.

Very reliable slag collection can thereby be facilitated.

In one embodiment, the measuring head cap is flush with the inflow conduit in immersion direction or covers the inflow conduit in immersion direction.

Covering the inflow conduit can also let the inflow opening remain not covered, e.g., due to the cap opening.

Very reliable slag collection can thereby be facilitated.

In an alternative embodiment, the inflow opening extends, protrudes and/or sticks out of the measuring head cap in immersion direction.

In one embodiment, the inflow conduit has an inflow opening being elevated towards the immersion direction relatively to the measuring element and/or extends above the immersion face of the housing. In other words, the inflow opening will arrive at the molten slag surface of the metal bath during immersion before the measurement element.

Thereby, prematurely chilling of the liquid slag by the measuring element can thereby be reduced and thus the ability of the molten slag to flow through the inflow conduit improved.

In one embodiment, the cap opening and/or the measuring head cap are arranged adjacent to the inflow opening and/or the inflow conduit. Preferably, the cap opening and/or the inflow opening are coaxially aligned and/or arranged over each other and/or crossing each other.

In one embodiment, the inflow opening, thus the opening of the inflow conduit in immersion direction, is greater than the cap opening or having a similar size.

In one embodiment, the inflow opening and the cup opening are positioned such that there is a minimal gap between the outer surface and/or curved surface of the inflow conduit and the measuring head cap and/or the cap opening.

Thereby, the fluid pressure of the molten slag exerted on the measuring head cap as it is pushed through the molten slag is directed to an inflow of the liquid molten slag into the inflow conduit and thus into the slag sample chamber.

In one embodiment, a housing is provided for embedding the internal portion of the inflow conduit, particularly including the end opposed to the inflow opening, the particularly entire slag sample chamber, and/or at least a part of the measuring element.

In particular, the selfsame housing is composed to embedding the internal portion of the inflow conduit and the slag sample chamber, particularly the entire slag sample chamber, and/or at least a part of the measuring element.

A very robust immersion device, very reliable with high functionality can be achieved.

In one embodiment, the housing comprises sand, resin sand and/or cement as embedding material. Protection from heat and/or fire can be obtained. The embedding material can be adhered together or being contained in a container for provided the three dimensional shape needed. Securing the embedded components and facilitating cooling of the slag sample can thereby be achieved.

In one embodiment, the inflow conduit is connected to the housing by means of cement. A very heat resistant connection can be obtained.

In one embodiment, the slag sample chamber for cooling and securing the slag comprises two half shells, which are held together by means of a tape, particularly made of paper, plastic or glass reinforced, and/or a clip, particularly made of a metal spring material.

Preferably, the slag sample container is contained at least partially within the device head.

In one embodiment, the sensor of the measuring element and/or the measuring element cap are arranged with a distance to the slag sample container in immersion direction. In a further embodiment, the measuring element is overlapping with the slag sample container in immersion direction, wherein the measuring element is extending beyond the top end of the slag sample container in immersion direction.

Both embodiments help to facilitate the division of the slag collection process and the molten metal measurement process.

In one embodiment, the slag sample chamber is made of or comprises metal and/or ceramic, preferably metal such as deep drawn galvanized steel. This helps to chill the molten slag and avoids destruction of the slag sample chamber.

In one embodiment, the outer portion of the inflow conduit is surrounded by gas in immersion direction from the housing before immersion. Before immersion has in this embodiment the meaning of before the tip of the immersion device has reached the molten metal surface. Inflow conduit from the housing in immersion direction means the outer portion of the inflow conduit, i.e., the part of the inflow conduit above the housing or the surface of it in immersion direction.

Very quick melting, melting away and/or melting down of the inflow conduit can be achieved.

Preferably, the outer portion of the inflow conduit has a funnel shape. This supports effective inflow of molten slag.

Preferably, at least half or the majority of the outer portion of the inflow conduit in immersion direction is neighboring on a same height or longitudinal position to the measuring element or a part of the measuring element.

Preferably, the maximal diameter of the outer portion of the inflow conduit composed to allow inflow of molten slag, i.e. without a protection cap to prevent entry of molten slag, amounts to at most 30% of the diameter of the measuring head.

In one embodiment, the inflow conduit has a diameter of at least 15% of a maximal cross section area of the immersion device. In particular, maximal cross section area corresponds to the maximal outer diameter of the immersion device, in particular the maximal outer diameter or outer diameter of the device head at an interface region to a cardboard tube as carrier tube for holding the device head of the immersion device during immersion. In particular, the maximal outer diameter of the immersion device is at least 50 mm and/or at most 80 mm.

In one embodiment, the inflow conduit is shorter than the slag sample chamber, particularly at least half of the length of the slag sample chamber and/or at most having the same length like the slag sample chamber.

In one embodiment, the inflow conduit has an internal volume of at least 10%, preferably at least 20%, and/or at most 100%, preferably at most 50%, of an internal volume of the slag sample chamber, particularly about or exactly 23%.

The previous two embodiments allow slag sample collection from the surface of molten metal with sufficiently large samples in a reliable manner.

In one embodiment, the not embedded and/or free standing outer portion of the inflow conduit is longer than the embedded internal portion of the selfsame inflow conduit and/or longer than the measuring element cap.

In one embodiment, the inflow conduit has an inflow opening in or being oriented in immersion direction, particularly while or during directing the molten slag to the slag sample chamber.

The inflow opening is thus forward of and not exposed to gases from e.g. a burning cardboard tube and thereby avoiding contamination of the collected slag sample. Very precise analysis results of the slag can be achieved.

In one embodiment, the inflow conduit and the measuring element and/or the inflow conduit and the measuring element cap are arranged next to each other or neighboring in immersion direction, thus both comprised by a cross section in a right angle to the longitudinal axis and/or immersion direction, preferably the cross section being within the top area of the immersion device.

Reliable sampling and measuring can thereby be achieved.

Preferably, in longitudinal section, the inflow conduit is arranged on one side of the longitudinal axis and the measuring element on the other side of the longitudinal axis. A longitudinal section is orthogonal to a cross section. A longitudinal section is in parallel to the longitudinal axis. A cross section has a right angle to the longitudinal axis.

In one embodiment, a vent channel is in gas communication to the slag sample chamber.

The Inflow of molten slag into the inflow conduit and the slag sample chamber can thereby be improved, especially for converter slag.

In one embodiment, the immersion device has a device head comprising the slag sample chamber, the inflow conduit and/or the measuring element. The device head usually further comprises the measuring head cap.

In one embodiment, the immersion device comprises a carrier tube or a cardboard tube as carrier tube to hold a device head, the device head comprising the slag sample chamber, the inflow conduit and the measuring element.

A multifunctional immersion probe suitable for sublance systems for use in refiners and converters can thereby be provided.

In one embodiment, the maximal outer diameter of the measuring head is equal or smaller than the maximal outer diameter of the carrier tube. In particular, the maximal outer diameter of the measuring head is equal or smaller than the outer diameter of the carrier tube at the interface to the device head.

A very compact sublance probe can thereby be provided.

Preferably, the measuring head has an interface means for connecting a carrier tube for holding the device head of the immersion device during immersion. In particular, the interface means can be a recess or ledge, preferably circumferentially. This allows a rapid removal of the device head from the immersion end of the carrier tube, thus avoiding cutting or breaking the tube to remove the solidified slag sample.

In one embodiment, a cardboard tube is used as a carrier tube for holding the measuring head of the sublance probe during immersion, in particular with an outer diameter of at least 50 mm and/or at most 80 mm.

In one embodiment, a feeding unit for feeding the immersion device and/or a control unit for controlling the feeding unit is provided for taking slag samples and/or conducting molten metal measurement in an automated or semi-automated manner.

In one embodiment, a sublance probe available for measuring metallurgical properties of molten metal during refining was modified to include the inflow conduit and slag sample chamber for collecting a slag sample. An immersion device for taking slag samples that can be produced at low costs as part of a sublance system utilizing sublance probes known to those skilled in the art for measuring metallurgical properties of molten metal during refining can be obtained.

Preferably, the inflow conduit and the measuring element and/or the inflow conduit and the measuring element cap are spaced from each other, thus not in an immediate contact, particularly with a distance of half the inflow conduit diameter or the measuring element cap or a measuring element housing.

Preferably, the inflow conduit, the measuring element and/or the measuring element cap are extending in parallel or substantially in parallel to the immersion direction of and/or the longitudinal axis.

In one embodiment, an immersion device for obtaining slag samples from a container of molten metal and slag for measuring metallurgical properties of the molten metal comprises a measuring head supporting one or more measuring elements to determine metallurgical properties of molten metals is fixed to the immersion end of a carrier tube, a sample chamber for receiving and cooling a slag sample, a slag inflow conduit dissolvable in molten metal and elevated in the immersion direction above all measuring elements for the purpose of collecting slag while passing through the slag layer.

It is thereby possible to provide a multifunctional measuring device that can obtain slag samples from the surface of molten metal that provide sufficiently large samples in a reliable manner through a small inflow conduit open to the slag layer in the direction of immersion.

A further aspect of the present invention relates to a method for collecting a slag sample and measuring a molten metal parameter. In the method, an immersion device, in particular the immersion device as described above, is immersed in immersion direction through a layer of molten slag into molten metal. During immersion through the layer of molten slag, molten slag is flowing into an inflow conduit facing in immersion direction and directing the molten slag to a slag sample chamber. At the moment of reaching the molten metal, the measuring head cap and the inflow conduit and then a cap covering the measuring element, which is also facing in immersion direction, melt such that the measuring element is exposed to the molten metal to conduct the measurement of the molten metal parameter.

Preferably, the immersion is a continuous movement, continuous feeding or continuous motion until the molten metal is reached. When reaching the molten metal, the movement, feeding or motion may rest for a while before the immersion device is pulled out, particularly again as a continuous movement, feeding or motion.

Generally, the immersion speed is chosen in a way that basically in the same moment of reaching the molten metal, thus less or far less than one second, the measuring head cap and the inflow conduit and then a cap covering a measuring element melt particularly down or away such that the measuring element is exposed to the molten metal to conduct the measurement of the molten metal parameter.

The above definitions and embodiments of the immersion device also apply for this method.

Reliable slag sampling and molten metal measurement also in a converter is achieved. Further advantages have been already described in the context of the immersion device.

The features of each embodiment as well as features of the above description and the features of the figure description can be combined with each other and combined with the subject matter of the aspects of the invention and each claim.

All combinations of one or more embodiments and/or aspects of the present invention with one or more claims are hereby disclosed.

Details and further advantages are provided in the figures, which depict a preferred execution example with the necessary details and individual components, and the associate detailed description.

Figure 2:
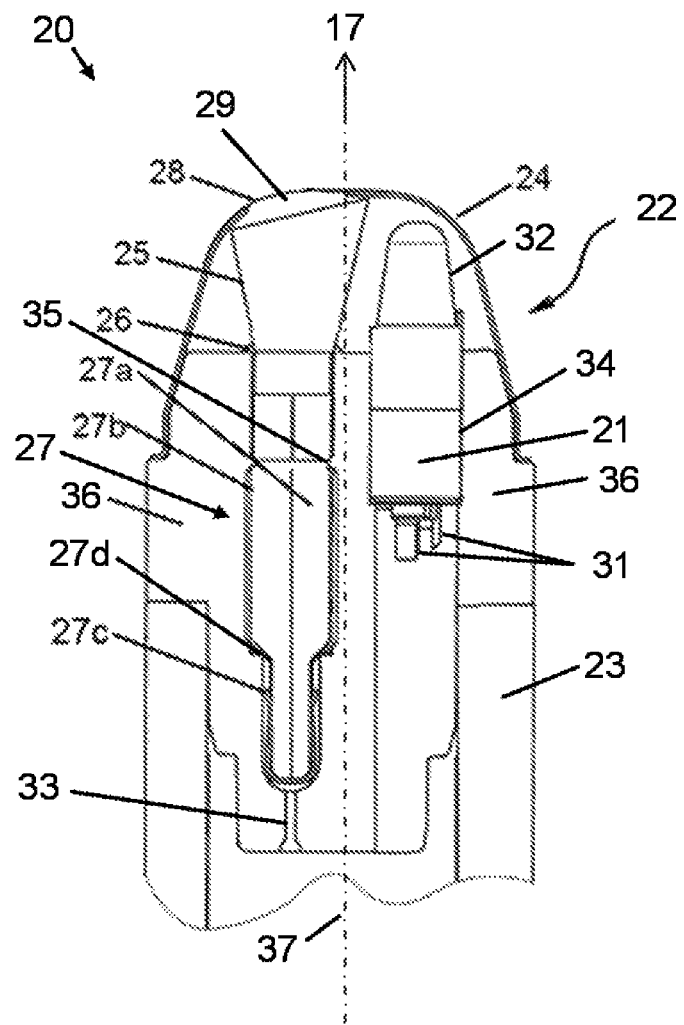
FIG. 2 shows a device head with one or multiple measuring elements mounted on a carrier tube, wherein an inverted conical inflow conduit extends from the slag chamber to the measuring head cap, in accordance with an embodiment of the present invention.
Figure 3:
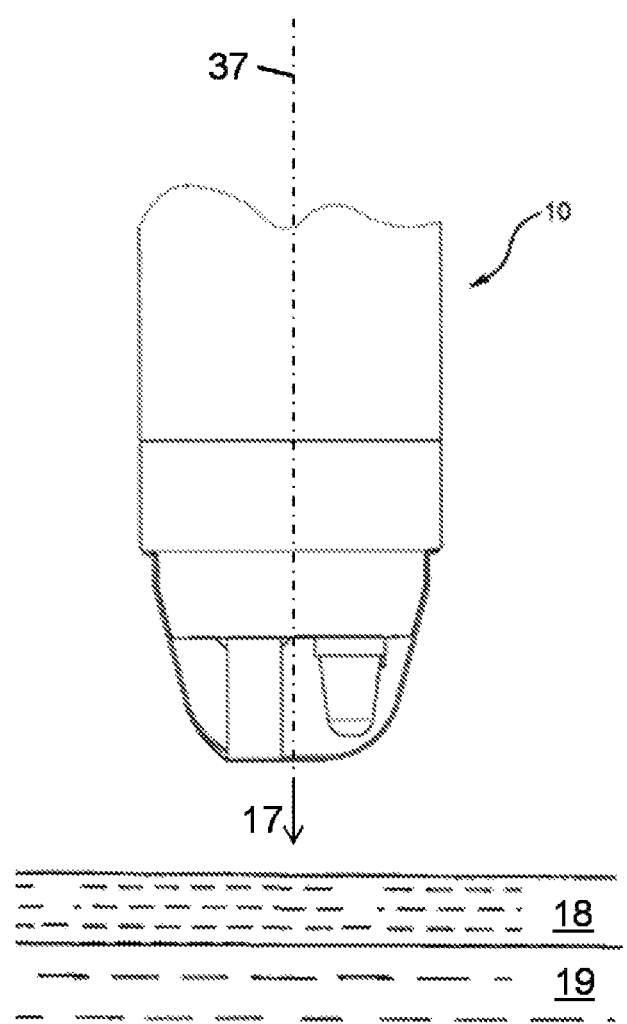
FIG. 3 shows the measuring head with a cut away of the measuring head cap, wherein the measuring head is orientated towards the immersion direction showing the respective layers of molten slag and molten metal, in accordance with an embodiment of the present invention.

The immersion devices 10, 20, exemplarily shown in FIGS. 1, 2 and 3, are used for taking a slag sample from a metallurgical vessel containing a layer of molten slag 18 floating on the molten metal 19. The device has a measuring head 2, 22, upon which are mounted one or multiple measuring elements 1, 21 (in FIGS. 1 and 2, they are hidden by a housing 14, 34) for determining one or more properties (i.e., parameter) of the molten metal 19.

The measuring head 2, 22 contains a slag sample chamber 7, 27 for receiving, cooling and retaining a slag sample with an inflow conduit 5, 25.

In one embodiment, the inflow conduit 5, 25 extends from a chamber opening of the slag sample chamber 7, 27 to a boundary of a measuring head cap 4, 24.

The measuring head cap 4, 24 is substantially covering the measuring head 2, 22. The measuring head 2, 22 is attached to the immersion end of a carrier tube 3, 23 (e.g., a cardboard tube), which serves to guide the measuring head towards immersion direction 17 into molten metal 19 passing through a layer of molten slag 18 which floats upon the molten metal 19.

As the measuring head is guided towards the molten slag surface, ambient heat of the metallurgical vessel increases the temperature of the measuring head cap 4, 24 thus avoiding its chilling effect upon the slag. The immersion device head cap 4, 24 has a cap opening 9, 29.

In one embodiment, the cap opening 9, 29 is covered by a tape 8, 28, particularly thin tape of preferably less than one millimeter in thickness and/or made of or comprising paper and/or plastic.

The tape is, in particular, composed to instantly burn upon exposure to the heated environment of the metallurgical vessel, thus enabling protection of the inflow conduit 5, 25 and the measuring element 1, 21 from pollution and contamination prior to immersion.

In one embodiment, the inflow conduit 5, 25 and/or the slag sample chamber 7, 27 have a straight shape and/or are rotationally symmetrically designed, preferably over its entire length.

The cap opening 9, 29 and the axis (i.e., long central axis) of the inflow conduit 5, 25 directly faces the layer of molten slag 18.

Upon immersion, molten slag 18 is forced into the inflow conduit 5, 25 as the device head is propelled in the immersion direction 17 towards the molten metal 19. The inflow conduit 5, 25 directs the molten slag 18 to the slag sample chamber 7, 27 for cooling.

The immersion process does not stop to collect slag 18 but continues uninterrupted towards the molten metal 19. While the slag inflow conduit 5, 25 is made of a thin metal which will melt relatively quickly upon exposure to the molten metal 19, it remains intact while passing through the molten slag layer.

Once the immersion device head passes into the molten metal 19, the measuring head protective cap 4, 24 and then a measuring element cap 12, 32 melt away substantially at the same time as the inflow conduit 5, 25 thus exposing at least one measuring element to the molten metal bath.

The measuring element 1, 21 or measuring elements 1, 21 can thus determine properties of the molten metal without influence of the thermal and chemical presence of the slag inflow conduit 5, 25. The temporary nature of the dissolvable slag inflow conduit 5, 25 provides a means of directing a sample of liquid slag 18 into the cooling slag sample chamber 7, 27 during immersion through the slag layer and then upon melting in the molten metal 19, does not interfere with subsequent measurements of the molten metal 19.

In one embodiment, the slag sample chamber 7, 27 has a bigger diameter than the inflow conduit 5, 25 and/or the inflow conduit 5, 25 is inserted into or surrounded by an upper portion of the slag sample chamber 7, 27. Very reliable guiding of the molten slag 18 into the slag sample chamber 7, 27 is obtained.

In one embodiment, the slag sample chamber 7, 27 comprises a narrowing 15, 35 (i.e., a waist) as a stopper for the inflow conduit 5, 25 during assembly. Very simple assembly is achieved.

FIG. 3 shows a particularly multifunctional immersion device orientated towards the immersion direction showing the respective the layers of slag and metal contained in a metallurgical vessel, the vessel itself is not shown. The terms "immersion direction" or "immersion end" or "towards immersion" are directional descriptions of the process of measuring. That is, the measuring device must be inserted into molten metal to be able to measure its properties such as temperature, oxygen content, and carbon content by solidification means, or collecting solid metal sampler for analysis, etc. Slag floats upon the molten metal such that to measure properties of the molten metal the measuring device 10 must first pass through the molten slag.

FIG. 1 shows a multifunctional measuring device 10 for collecting a slag sample and measuring a molten metal parameter comprising a device head 2 with a housing 16, preferably made of resin sand and/or a ceramic material. The measuring head 2 is attached to the immersion end of a carrier tube 3.

In particular, the carrier tube 3 is typically a heavy walled cardboard tube with an outside diameter between 50 and 80 mm. Within and/or partially surrounded by the housing 16 is a slag sample chamber 7 for receiving a sample of molten slag 18.

The slag sample chamber 7 is ventilated by exhaust conduit or a vent channel 13. The slag sample chamber 7 is typically formed of two mating halves 7a, 7b, particularly in a clam shell fashion and/or for ease of handling and use held together by tape 7c and/or metal spring clips 27c (not shown in FIG. 1). The material of the mating halves is typically metal, ceramic and/or a mixture thereof.

Both the internal and external shape of the assembled slag sample chamber 7 is not specific to the invention and maybe configured to a variety of shapes and sizes known to those skilled in the art. The slag sample chamber 7 on its immersion direction 17 has a chamber opening for receiving the slag inflow conduit 5 which is preferably cemented to the housing 16 particularly by a refractory cement 6.

The slag inflow conduit 5 extends from the slag sample chamber 7 to a cap opening 9 in the measuring head cap 4. In particular, the measuring head cap 4 is made of a metal that will not melt upon contact with the slag 18 but is readily melted by contact with the molten metal 19.

The cap opening 9 of the immersion device head cap 4 as well as an inflow opening of the inflow conduit 5 are covered by the tape 8.

In one embodiment, thus not specific to one of the shown embodiments, the slag inflow conduit 5, 25 and the cap opening 9, 29 are positioned such that there is a minimal gap between the opening and the outer wall of the inflow conduit 5, 25 such that the fluid pressure of the molten slag 18 exerted on the measuring head cap 4 as it is pushed through the slag 18 is directed to an inflow of the liquid slag 18 into the inflow conduit 5, 25 and thus into the slag sample chamber 7, 27.

Preferably the inflow conduit 5 is metal, more preferably low carbon steel in the present example of a device for use in a steelmaking converter. The wall thickness of the inflow conduit 5 is usually between 0.5 and 3 mm, preferably 1.5 mm. The internal volume of the slag conduit 5 is between 10 and 100%, preferably between 20 and 50%, of the internal volume of the slag sample chamber 7, preferably 23%.

As the measuring head is further pushed past the slag layer and into the molten metal bath, the measuring head cap 4 and the inflow conduit 5 melt. The inflow conduit 5 melts back towards the housing 16 particularly to approximately the area of the cement 6 for connecting the inflow conduit 5 to the housing 16, thus the surface of the housing 16 in immersion direction 17. Thereafter, the measuring element cap 12 melts exposing one or more molten metal measuring elements 1 (not shown) housed in the housing 14.

Electrical signals from the measuring element 1, 21 or measuring elements 1, 21 are in both shown exemplarily embodiments of an immersion device 10, 20 relayed from contacts 11, 31 particularly by wiring (not shown) to remote instrumentation.

After measuring the properties of the molten metal 19, the carrier tube 3, 23 and attached measuring head 2, 22 are withdrawn from the metallurgical vessel.

The slag sample chamber 7 secures the slag sample during withdrawal and is removed from the measuring head 2 and carrier tube 3 in the immersion direction 17. In particular, the immersion direction 17 is in parallel to the longitudinal axis 37 of the measuring head 2, which is in particular having a curved surface and/or a substantially cylindrical shape. Preferably, the outer curved surface of the measuring head 2 flushes with the outer curved surface of the carrier tube 3.

FIG. 2 shows another embodiment of a particularly multifunctional immersion device 20 for collecting a slag sample and measuring a molten metal parameter comprising a measuring head 22 with a housing 36, preferably made of resin sand but can also be a ceramic material or a mixture thereof. The measuring head 22 is attached to the immersion end of a carrier tube 23. The measuring head 2 has a portion extending outwardly towards the immersion direction 17 and has a portion within the carrier tube 23, opposite the immersion direction. In particular, the immersion direction 17 is in parallel to the longitudinal axis 37 of the measuring head 22, which is in particular having a curved surface and/or a substantially cylindrical shape. Preferably, the outer curved surface of the device head 22 flushes with the outer curved surface of the carrier tube 23.

In particular, the carrier tube 23 is typically a heavy walled cardboard tube with an outside diameter between 50 and 80 mm. Within and/or partially surrounded by the measuring head 22 is a slag sample chamber 27 for receiving a sample of molten slag 18. The slag sample chamber 27 maybe ventilated by exhaust conduit or vent channel 33. The slag sample chamber 27 is typically formed of two mating halves 27a, 27b, particularly in a clam shell fashion and/or for ease of handling and use held together by a metal spring clip 27c.

In one embodiment, the slag sample chamber 27 has two sections along the longitudinal axis 37 with different diameters.

Preferably, the section in immersion direction has the bigger diameter compared to the other section. This makes it possible to simply provide a circumferential step 27d, shoulder or ledge for resting on an edge in the device head 22 or housing 36.

A gap surrounding the other section of the slag sample chamber 27 can thereby be realized to enable the space and use of the clip 27c that clamps at one end of the slag sample chamber 27, particularly opposed to the immersion direction 17, both halves 27a, 27b together.

The material of the mating halves 27a, 27b is typically metal, ceramic and/or a mixture of part metal, part ceramic. Both the internal and external shape of the assembled slag sample chamber 27 are not specific to the invention and maybe configured to a variety of shapes and sizes known to those skilled in the art.

The slag sample chamber 27 on its immersion direction 17 has a chamber opening for receiving the slag inflow conduit 25 which is preferably cemented to the device head 22 or the housing 36 by a refractory cement 26.

The slag inflow conduit 25 extends from the slag sample chamber 27 to cap opening 29 in the measuring head cap 24. The measuring head cap 24 is preferably made of a metal that will not melt upon contact with the molten slag 18 but is readily melted by contact with the molten metal 19.

The cap opening 29 of the measuring head cap 24 is covered by a tape 28, which is in particular thin and/or made of or comprising paper and/or plastic.

In particular, the slag inflow conduit 25 is of an inverted conical shape, preferably larger at the immersion end than at its opposite end adjacent to the chamber opening.

In one embodiment, the immersion end of the inflow conduit 25 is greater than the cap opening 29 of the measuring head cap 24 and/or meets the measuring head cap 24.

In one embodiment, thus not specific to one of the shown embodiments, the inflow conduit 5, 25 is positioned such that there is a minimal gap between the measuring head cap 4, 24 and the extremity of the inflow conduit 5, 25 such that the fluid pressure exerted on the measuring head cap 4, 24 as it is pushed through the slag 18 is directed to an inflow of the liquid slag 18 into the inflow conduit 5, 25 and thus into the slag sample chamber 7, 27.

Preferably the inflow conduit 25 is metal, more preferably steel. Preferably the inflow conduit 25 is metal, more preferably low carbon steel in the present example of a device for use in a steelmaking converter. In particular, the wall thickness of the inflow conduit 25 is between 0.5 and 3 mm, preferably 1.5 mm. Preferably, the internal volume of the slag inflow conduit 25 is between 10 and 100%, preferably between 20 and 50%, of the internal volume of the slag sample chamber 27, preferably 23%.

As the measuring head 22 is further pushed past the slag layer and into the molten metal bath, the inflow conduit 25 melts back towards the housing 36 to approximately the area of the cement 26 connection to the inflow conduit 25, thus the surface of the housing 36 in immersion direction 17.

In particular, the immersion device can be used in a converter and refiner system, but may be used in other metal refining vessels such as an electric arc furnace but in particular not in a blast furnace.

In general, standard sublance sensors, which is a typical expression also for the present immersion device or measuring head, are foreseen with a package of capping. Most sensors carry multiple caps. The smallest caps serve to protect against impact and handling during the assembly phase of the sensor.

The wall thickness of such cap is typically around 0.2 mm. In contact with slag, it only takes a few seconds to melt. In contact with steel, it takes about 0.2 seconds to melt. The outer big cap 4, 24 serves as protection during transportation and handling of the sensor and protection against bigger impacts. The wall thickness of such a cap is around 0.8 mm. In contact with slag, it takes several seconds to melt. In contact with steel, it takes about 1 second to melt.

Sublance sensors are often foreseen with means to prevent slag sticking to this cap. An additional paper cap is the most common used protection.

Preferably, a thin Zn coating (5 µm) that will evaporate around the time the cap reaches 907° C. can be used. This creates a lot of gases that create a small explosion that blows all slag sticking on the cap away.

The slag sample preferably weighs around 30 g, resulting in a volume of about 20 cc. A range for the weight and/or volume may be plus and/or minus 10% or 20%.

A sublance sensor is usually designed to last one measuring cycle. This means the sensor travels in the bath typically with an entry speed of 30-60 cm/s, it stays stationary during 6-8 seconds, and then leaves at a speed of 20 cm/s.

The typical immersion depth in the steel is about 40 cm and the layer of slag is about 30 cm when not foaming. Generally, it can reach a few meters in case it is foaming.

Based on these values, the sensor will travel through the slag layer during about 1 second, it will continue to travel to its deepest position during 1.5 seconds, it will stay stationary during 6 seconds, and travel back up to the bath level during 1.5 seconds.

The thermocouple is registering the temperature in a continuous way during the total immersion time. This allows to interpret the temperature correctly after the sensor arrived in its deepest position and the hot junction of the thermocouple has been heated to the bath temperature. This is typically after 3-4 seconds at stationary position.

All thermal mass such as sample inlets disturb the bath by cooling. The present invention uses in an embodiment an inlet that will dissolve in the bath and does not influence the thermal condition of the bath as soon as the outer cap has opened.

During the immersion of the sensor at the moment the tip of the sensor touches the slag layer for the first time, all gases in the filling path of the slag sampler will heat and start to expand, fully heated this is a volume factor six. This gas expansion creates a counter pressure in the slag sampler, while the pressure due to immersion should be considered very low. As a consequence the expanding gas tends to spit the slag back in the bath.

Because the slag can only be collected while travelling through the slag layer, preferably a lot of ventilation needs to be created. This ventilation should be as much as possible without creating holes that allow the slag to flow out of the sample cavity.

The wall thickness of the inlet conduit should be chosen as function of the wall thickness of the outer steel cap. The preference is that it is less or equal than the wall thickness of the cap.

The volume from the conduit should be as big as possible as long as the enclosed air can escape through the vent holes of the sample cavity. As an example it is preferably more than 10% and/or up to 100%, particularly between 20% and 50%.

Furthermore air vent in the inlet conduit are considered as advantage, all to minimize the pressure buildup during immersion.

Multiple variations and modifications are possible in the embodiments and between the aspects of the invention and the embodiments of the invention described herein and thereby covered by the scope of the invention. In some instances, some features of the present invention may be employed without a corresponding use of the other features. Accordingly, it is appropriate that the foregoing description be constructed broadly and understood as being given by way of illustration and example only.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. Immersion device (10, 20) for collecting a slag sample and measuring a molten metal parameter, the immersion device (10, 20) comprising:
    an inflow conduit (5, 25) for directing molten slag (18) to a slag sample chamber (7, 27); and
    a measuring element (1, 21) for measuring the parameter of the molten metal (19),
        wherein the inflow conduit (5, 25) comprises an external portion and an internal portion,
        wherein the inflow conduit (5, 25) and the measuring element (1, 21) are both arranged in a top area of an immersion end of the measuring head (2, 22) and/or are both facing towards an immersion direction (17),
        wherein the immersion device (10, 20) is composed such that during immersion in the immersion direction (17) into the molten slag (18) and then the molten metal (19), the molten slag (18) enters the external portion of the inflow conduit (5, 25) and is directed through the inner portion of the inflow conduit (5, 25) to the slag sample chamber (7, 27), and
        wherein the inflow conduit (5, 25) is composed such that the inflow conduit (5, 25) resists molten slag (18) but melts upon exposure to the molten metal (19).

2. Immersion device (10, 20) of claim 1, wherein the external portion of the inflow conduit (5, 25) is free standing.

3. Immersion device (10, 20) of claim 1, further comprising a measuring head cap (4, 24) for covering the top area of the immersion device (10, 20), wherein the measuring head cap (4, 24) is composed such that the measuring head cap (4, 24) resists molten slag (18) but melts upon exposure to the molten metal (19).

4. Immersion device (10, 20) of claim 3, wherein a cap opening (9, 29) of the measuring head cap (4, 24) is designed such that molten slag (18) flows through the cap opening (9, 29) into the inflow conduit (5, 25).

5. Immersion device (10, 20) of claim 3, wherein the measuring head cap (4, 24) is flush with the inflow conduit (5, 25) in the immersion direction (17) or covers the inflow conduit (5, 25) in the immersion direction (17).

6. Immersion device (10, 20) of claim 1, wherein the inflow conduit (5, 25) has an inflow opening oriented in the immersion direction (17).

7. Immersion device (10, 20) of claim 1, further comprising a housing (16, 36) for embedding the internal portion of the inflow conduit (2, 25) and/or the slag sample chamber (7, 27).

8. Immersion device (10, 20) of claim 7, wherein the outer portion of the inflow conduit (5, 25) is surrounded by gas in the immersion direction (17) from the housing (16, 36) before immersion.

9. Immersion device (10, 20) of claim 1, wherein the inflow conduit (5, 25) and the measuring element (1, 21) are arranged next to each other in the immersion direction (17).

10. Immersion device (10, 20) of claim 1, wherein the inflow conduit (5, 25) has a diameter of at least 15% of a maximal cross section area of the immersion device (10, 20).

11. Immersion device (10, 20) of claim 1, wherein the inflow conduit (5, 25) has an internal volume of at least 10% and/or at most 100% of an internal volume of the slag sample chamber (7, 27).

12. Immersion device (10, 20) of claim 1, further comprising a vent channel (13, 33) in gas communication with the slag sample chamber (7, 27).

13. Immersion device (10, 20) of claim 1, further comprising a carrier tube (3, 23) or a cardboard tube as carrier tube (3, 23) to hold a measuring head (2, 22), the measuring head (2, 22) comprising the slag sample chamber (7, 27), the inflow conduit (5, 25) and the measuring element (1, 21).

14. Method for collecting a slag sample and measuring a molten metal parameter, the method comprising:
immersing an immersion device (10, 20) in an immersion direction (17) though a layer of molten slag (18) into molten metal (19),
wherein during immersion through the layer of molten slag (18), molten slag (18) is flowing into an inflow conduit (5, 25) facing in the immersion direction (17) and directing the molten slag (18) to a slag sample chamber (7, 27),
wherein in the moment of reaching the molten metal (19), a measuring head cap (4, 24) and the inflow conduit (5, 25) and then a cap (4, 24, 12, 32) covering a measuring element (1, 21), which is also facing in the immersion direction (17), melt such that the measuring element (1, 21) is exposed to the molten metal (19) to conduct the measurement of the molten metal parameter.

\* \* \* \* \*